United States Patent [19]
Lautenschläger

[11] Patent Number: 5,725,835
[45] Date of Patent: Mar. 10, 1998

[54] DEVICE FOR INITIATING AND/OR PROMOTING CHEMICAL OR PHYSICAL PROCESSES IN A MATERIAL

[76] Inventor: Werner Lautenschläger, Waldstrasse 15, D-88299, Leutkirch, Germany

[21] Appl. No.: 646,232

[22] PCT Filed: Nov. 11, 1994

[86] PCT No.: PCT/EP94/03742

§ 371 Date: May 9, 1996

§ 102(e) Date: May 9, 1996

[87] PCT Pub. No.: WO95/13133

PCT Pub. Date: May 18, 1995

[30] Foreign Application Priority Data

Nov. 11, 1993 [DE] Germany ............... 4338583.4
Jun. 3, 1994 [DE] Germany ............... 4419590.7

[51] Int. Cl.⁶ .............................. B01J 10/00; B01J 19/08
[52] U.S. Cl. ............... 422/129; 422/186; 422/186.29; 422/295
[58] Field of Search ............... 422/21, 129, 186, 422/186.29, 295

[56] References Cited

U.S. PATENT DOCUMENTS

| | | | |
|---|---|---|---|
| 4,051,382 | 9/1977 | Ogawa et al. | 250/531 |
| 5,230,865 | 7/1993 | Hargett et al. | 422/102 |
| 5,246,674 | 9/1993 | Katschnig et al. | 422/302 |
| 5,320,804 | 6/1994 | Zakaria et al. | 422/21 |
| 5,338,409 | 8/1994 | Heierli | 202/205 |
| 5,345,066 | 9/1994 | Knapp et al. | 219/686 |
| 5,369,034 | 11/1994 | Hargett et al. | 436/155 |
| 5,382,414 | 1/1995 | Lautenschlager | 422/186 |
| 5,383,414 | 1/1995 | Winter et al. | 112/162 |
| 5,387,397 | 2/1995 | Strauss et al. | 422/129 |

FOREIGN PATENT DOCUMENTS

| | | |
|---|---|---|
| 0416759A1 | 11/1991 | European Pat. Off. . |
| 0569265A1 | 11/1993 | European Pat. Off. . |
| 3141939A1 | 5/1983 | Germany . |
| 4038273A1 | 11/1990 | Germany . |
| 3933992A1 | 4/1991 | Germany . |
| 4102129A1 | 7/1992 | Germany . |
| 4114525A1 | 8/1992 | Germany . |
| 2102402 | 2/1981 | United Kingdom . |
| WO9322650 | 11/1993 | WIPO . |

OTHER PUBLICATIONS

"Microwave–Assisted Extration of Organic Compounds from Standard Reference Soils and Sediments", V. Lopez–Avila, et al., ANALYTICAL CHEMISTRY, Apr. 1994, Vol. 66, No. 7.

*Primary Examiner*—Nina Bhat
*Attorney, Agent, or Firm*—Fitzpatrick, Cella, Harper & Scinto

[57] ABSTRACT

A device for initiating and/or promoting chemical or physical processes in a material, or specimen material, in which the material is heated in a reaction chamber (2) which is heatable by a heating means (3), in particular a microwave heating means, and thereby subjected to pressure, the material is firstly exposed to an initial pressure in the reaction chamber (2) and is then heated.

25 Claims, 4 Drawing Sheets

1

DEVICE FOR INITIATING AND/OR PROMOTING CHEMICAL OR PHYSICAL PROCESSES IN A MATERIAL

BACKGROUND OF THE INVENTION

1. Field of the Invention

The invention relates to a microwave heating device and more it concerns novel arrangements for moving a container for materials to be heated between loading and heating positions.

DESCRIPTION OF THE RELATED ART

In analytical chemistry and in particular for the preparation of materials, preferably specimen materials, or for the transformation of initial materials into reaction products it is common practice to perform the treatment under heat and pressure (excess pressure) as the desired process can only be realized or improved or forced under these conditions.

In a device are described in the DE-A-39 33 992, by irradiation of a gas under pressure with long wavelength electromagnetic waves a shorter wavelength radiation is generated with which the initial materials are irradiated, or the initial materials themselves are placed under reduced pressure and are irradiated directly with the long wavelength electromagnetic waves. For this purpose there serves a device with a heating chamber surrounded by a housing on all sides and closeable in a sealed manner in which an initial material introduced into an open or closeable receptacle can be heated under reduced pressure which is generated by an air pump connected with the heating chamber (FIG. 1 and 4) or, in the case of a closeable receptacle, connected with the receptacle (FIG. 2 and 3 of this publication) by means of an evacuation line.

A device of the kind mentioned in the introduction can be found in DE 40 38 273 A1 in various configurations in which, for the purpose of opening a housing surrounding the reaction chamber, the side wall (FIG. 1), lid (FIG. 2) or base (FIG. 3) of the housing in DE 40 38 273 A1 is displaceable by means of a displacement device between the closed position and an open position. There is arranged, on the respective wall part of the housing which is to be opened, a mounting, e.g. a locating plate, for at least one specimen receptacle, so that the latter can be moved into the reaction chamber or out of it with the respective displacement movement of the wall part. Through this the placement and removal of at least one specimen receptacle in the reaction chamber or the housing is facilitated, but a special mounting for the at least one specimen receptacle is necessary. Also a simple positioning of the specimen receptacle(s) on the floor of the housing is not possible. Furthermore on account of the presence of the mounting device and also for further constructional reasons this known device is not constructed in a way that would allow the placing of the specimen material directly in the housing, i.e. without a special specimen receptacle. A further disadvantage of the known device is to be seen in that in the configuration with a liftable lid for the reaction chamber (FIG. 2) the accessability to the reaction chamber is very much restricted in the open position: although the lid is lifted from the housing, because of its position above the housing the accessability of the upperside housing opening is made more difficult.

A device of the kind under consideration can be found in WO/93/22650 in several configurations, in which, for receiving several pot-like specimen receptacles, a mounting device is provided in the form of a rotor in a reaction chamber, whereby the specimen receptacle can be inserted, by a horizontal movement, between a positioning plate engaging below the specimen receptacle and a lid which engages above the specimen receptacle—with its upper side opening—thereby effecting closure. The latter lid is part of the mounting device, which remains on the mounting device upon removal of the specimen receptacle. With this known device it is necessary to manually grasp the specimen receptacle upon insertion or withdrawal from the mounting device, which is possible only with difficulty in particular after the material treatment if only on account of the increased temperature. Furthermore it must be taken into consideration that the specimen material must be inserted into the mounting device purposively. Furthermore this known device is not suitable for a reaction chamber of larger dimensions, as manual handling is not possible on account of the resulting weight. In the event that several specimen materials are to be treated simultaneously several specimen receptacles are therefore required with this known configuration, which must be purposively inserted into their working positions with respective horizontal movements and withdrawn again after the treatment.

SUMMARY OF THE INVENTION

The object of the invention is further to configure a device of the kind mentioned in the introduction in such a way that a more simple loading of the reaction chamber is possible.

This object is by means of a generally horizontal guide for displacing a material containing housing underpart relative to a lid after a lifting device has begun to lift the lid from a closed or working position and a ready position.

With this embodiment according to the invention the housing underpart which encloses the reaction chamber or its lid is displaceable into an opening ready position not only by means of a lifting device, but the housing underpart or the lid is also displaceable approximately horizontally into a loading position and back again, so that the accessability of the reaction chamber is significantly improved and thus the specimen material or specimen materials can be placed directly or in specimen receptacles into the reaction chamber in a simple and ready way. The displacement of the lid or the housing underpart can be effected manually or by means of a motorised drive. For the approximately vertical displacement of the lid or the housing underpart a motorised drive is advantageous, as the weight involved must be overcome. Furthermore, such a displacement device can at the same time form the closure device for the housing. For the approximately horizontal displacement of the lid or the underpart of the housing a manual displacement in a guide is advantageous for the purpose of simplification of the device and its control.

In the subclaims there are features which contribute to achievement of the object, simplify construction, make possible a simpler, faster and thus more economical and reliable treatment, improve energy consumption and economy and make possible an advantageous and reliable control of the treatment process.

Further, the invention relates to a particular construction of the device which is distinguished not only by a simple and economical and compact construction, and convenient operation, but also ensures a high degree of utilization of the heating energy and can thus be operated economically and reliably.

Furthermore, the invention relates to a further advantageous construction, in which the pressure regulation elements of the device are arranged in a particular constructional component which is separate from the reaction chamber, which may be connected with the reaction chamber merely by means of a connecting line, and to advantageous arrangements of pressure control elements such as valves, which ensure a trouble-free and reliable process development.

BRIEF DESCRIPTION OF THE DRAWINGS

Below, the invention and further advantages achievable thereby will be described in more detail with reference to preferred exemplary embodiments and to the drawings, in which.

DETAILED DESCRIPTION OF THE PREFERRED EMBODIMENTS

Figure 1:
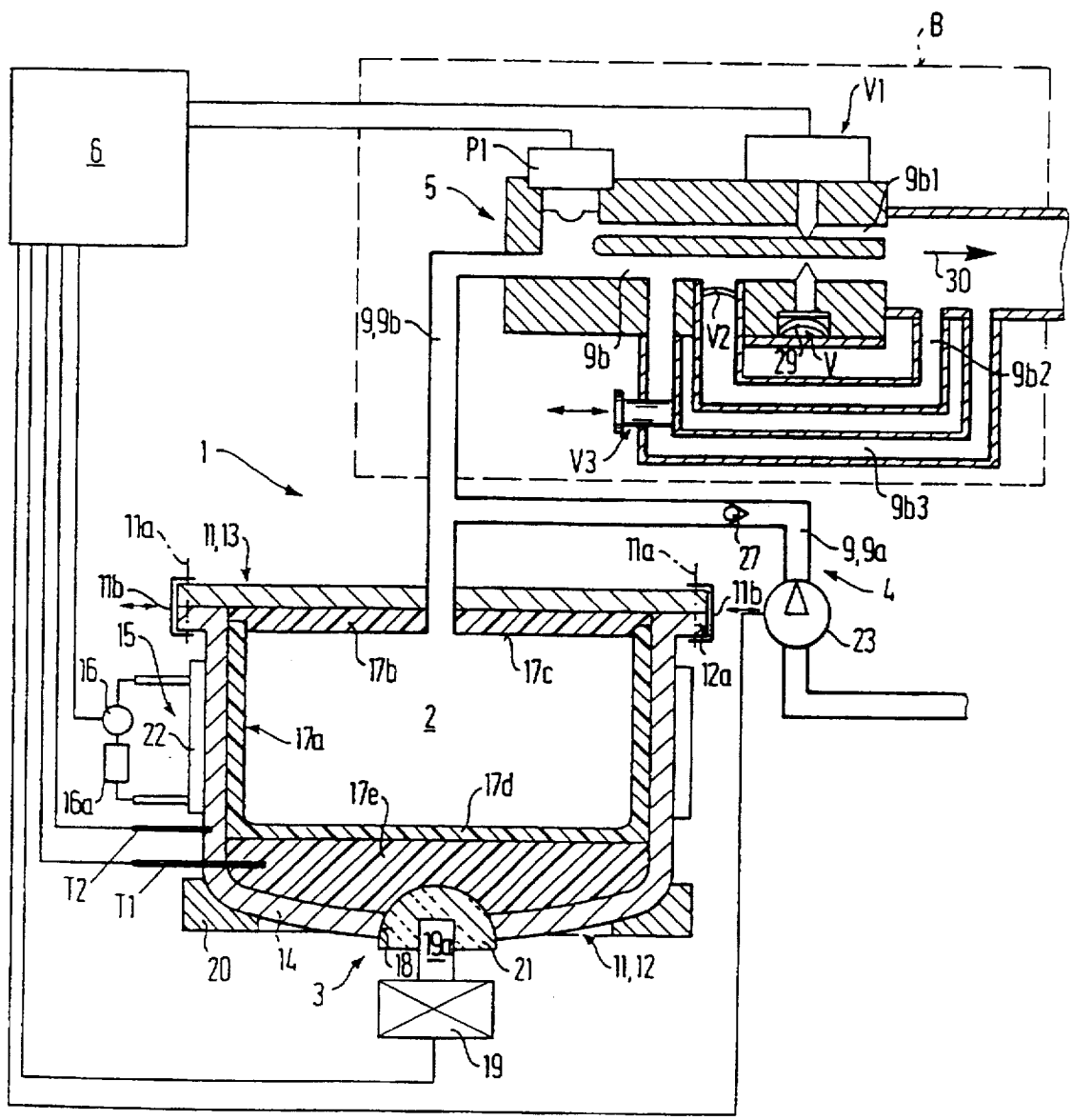
FIG. 1 is a device with a reaction chamber according to the invention in largely schematic sectional side view.

The main parts of the device which is generally designated as 1, are the reaction chamber 2, a heating device 3, in particular a microwave heating device, for the reaction chamber 2, a pressure loading device 4 for the reaction chamber 2, a pressure control block 5 for controlling the pressure in the reaction chamber 2, and a control device 6 for the functional control of the device 1, here in particular the heating device 3 and the pressure acting, whereby the respective associated addressable control parts are connected by means of control lines of the control device 6.

The material to be treated can be placed either directly or in one or in several receptacles in the reaction chamber 2. Insofar as one or several receptacles 7 (FIG. 2) are available, it may be advantageous for handling reasons to associate a carrier frame, in particular of plastics or microwave permeable or semi-permeable material, with the receptacle(s) 7, with which they may be readily placed in the reaction chamber 2 and removed again.

For this purpose the reaction chamber 2 has an upper loading opening for the introduction and removal of the material to be treated.

In the present embodiment the device 1 is a microwave-autoclave functioning with high temperature and high pressure for the treatment or preparation of materials, in particular specimen materials for analysis purposes.

For controlling the pressure in the reaction chamber 2 several valves are provided, which are arranged in the separately arranged control block 5 which is connected with the reaction chamber 2 by means of a connecting line 9, which may be either a rigid or a flexible pipeline or a hose line, in particular of plastics.

The reaction chamber 2 is surrounded by a housing 11, which for the purpose of loading the reaction chamber 2 is preferably formed of a pot-shaped housing underpart 12 with an edge flange 12a and a preferably substantially flat lid 13 which is detachably fastenable to the housing underpart 12. The fastening device for the lid 13 on the housing underpart 12 is not illustrated for reasons of simplicity. It may comprise either screws 11a which are schematically illustrated or oppositely arranged locking ring halves 11b of U-shaped cross-section which, horizontally opposed to one another, are moveable between a closing position (shown) in which they engage above the lid 13 and below the edge flange 12a and an outwardly offset release position (not shown) either by hand or by a motorised drive.

The housing 11 is a metal housing. The microwave coupling into the housing 11 is effected from below through a base 14 of the housing, which base is preferably arched downwardly. A cooling device generally designated as 15 is associated with the housing 11, which has one or several cooling lines or cooling channels arranged either inside or outside along the walls of the housing 11, through which a coolant, in this case water, is delivered by means of a pump 16 and can be cooled in a cooler 16a.

The housing 13 is preferably lined on the inside with a corrosion and heat resistant and preferably also heat-insulating lining material. With the present exemplary embodiment a pot-like lining part 17a which is adapted to the inner profile of the housing underpart 12 and a lining lid plate 17b arranged on the lower side of the lid 13 are provided, which lining lid plate preferably engages into the lining part 17a with a projection 17c projecting downwardly.

Preferably there is present between the base part 17d of the lining part 17a and the base 14 of the underpart 12 of the housing an additional plate-shaped lining base part 17e of microwave permeable material and/or plastics. For coupling the microwaves a preferably central opening 18 is provided in the base 14, in or below which a magnetron 19 or a waveguide or an associated radiation element such as an antenna 19a is arranged. On the upper edge of the opening 18 a bowl-shaped or hollow-ball section-shaped radiation element 21 of microwave-permeable material, preferably quartz, is arranged which is positioned in a correspondingly formed recess of the base part 17e. There may also be provided a radiation element in the form of a cylinder having a vertical axis, into which the antenna 19a penetrates in an aperture with play for movement.

A supporting part for the housing 11 is designated as 20, on which the housing is arranged and, if appropriate, fastened.

Figure 2:
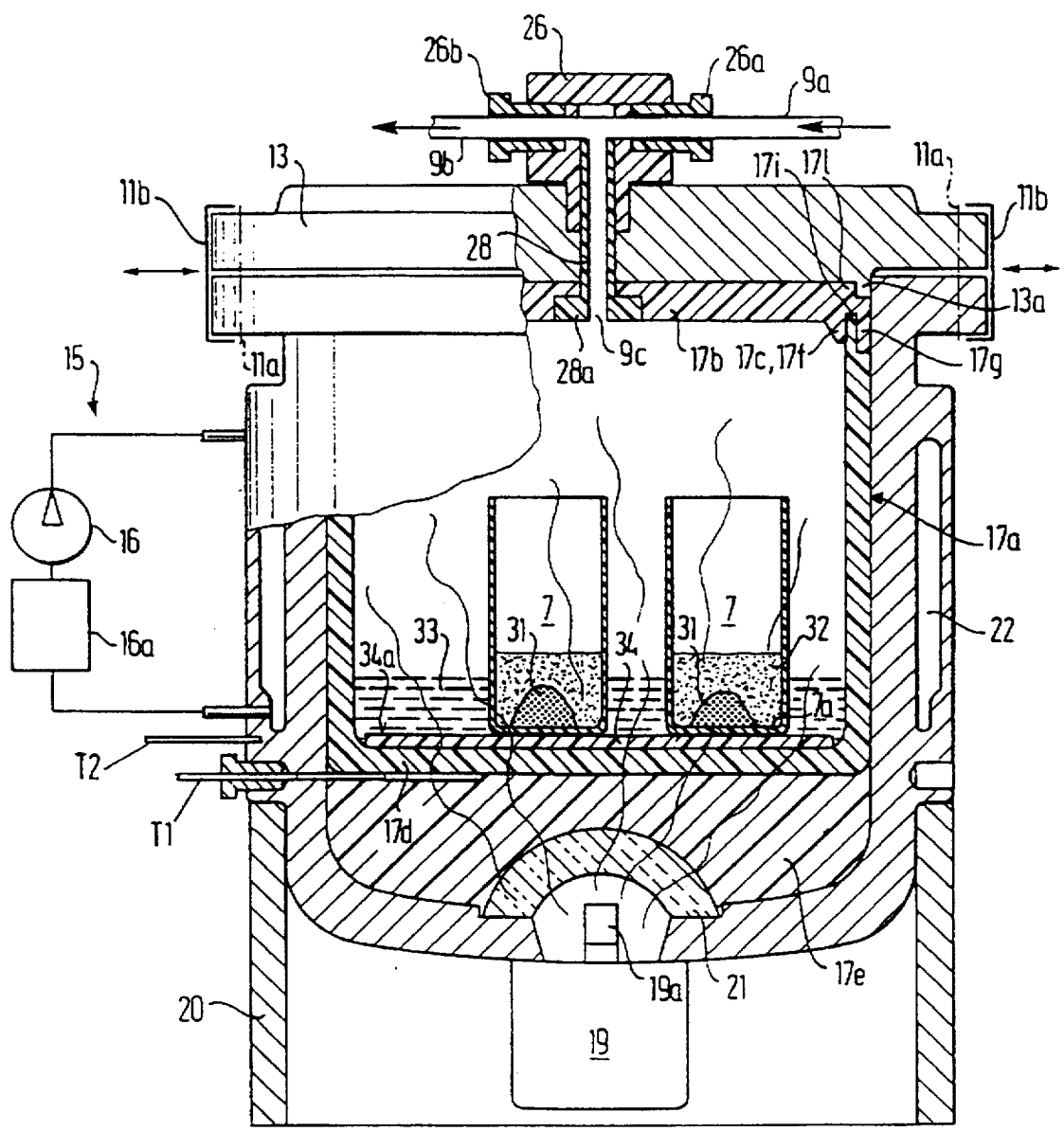
FIG. 2 is an exemplary embodiment of the reaction chamber of the device of FIG. 1 in a vertical sectional view and to a larger scale.

In the exemplary embodiment in accordance with FIG. 2 there is provided, to improve the sealing between the lining lid plate 17b and the upper edge of the lining part 17a, a sealing lip 17f, which is formed preferably in one piece on the lid plate 17b and engages into the lining part 17a and sealingly bears against the inner wall thereof. The lid plate 17b can also engage over the upper edge of the lining part 17a on the outside, in this case by means of an annular projection 17g projecting downwardly, which engages into an outer recess of corresponding cross-section on the upper edge of the lining part 17a. This upper edge 17a is thus tapered and engages into a corresponding annular groove 17i in the lid plate 17b.

In the present embodiment in particular the base region of the housing 11 is well heat-insulated by means of the base part 17d and the additional base part 17e. Therefore the cooling device 15 is arranged merely laterally next to the reaction chamber 2 in or on the sheath of the housing underpart 12, here in the form of an annular cooling channel 22 in the wall of the housing underpart 12 which in the present case is preferably circular in horizontal cross-section.

Preferably the lid plate 17b sits on the lid 13 with an upper-side centering member $17_1$ in a corresponding lower-side recess. Furthermore, the lid 13 has a lower-side centering member 13a, in the present case a centering ring, which engages into the circumferential wall of the housing underpart 12 thus centering the lid 13 in its closed position.

In the region of the housing 11 two temperature sensors T1, T2 are provided. The first temperature sensor T1 is in the base region of the housing underpart 12 and serves for determining actual values for the regulation of the heating power and thus also of the temperature in the reaction chamber 2.

The second temperature sensor T2 serves for determining the sheath temperature of the housing 11 and for the regulation of the cooling device 15, for the purpose of preventing an overheating of the material of the walls of the housing.

The connecting line 9 is connected with the upper region of the reaction chamber 2, whereby it penetrates the lid 13 preferably centrally in the present embodiment. A relatively thin nominal cross-section suffices for the connection line 9. Preferably this nominal cross-section is approx. 6 mm, whereby the connecting line 9 can preferably be a flexible line of plastics, in order to be able to move the lid 13 on closing and opening.

With the exemplary embodiment in accordance with FIG. 2 the connection line 9 branches in a T-shaped fitting 26 which is fitted or screwed into the housing 11, from above, here into the lid 13, from which a connection line branch 9a extends to the loading device 4 and the other connection line branch 9b extends to the control block 5. In the first-mentioned connection line branch 9a there are arranged an air- or gas pump 20 and a non-return valve 27 which opens in a flow direction towards the reaction chamber 2 and closes in the opposite direction. In the present embodiment the feed-through channel 9c, which forms the common connection line section—here in the lid 13, is lined with a sleeve 28, preferably with an inner flange 28a, of temperature and corrosion-resistant material, preferably plastics. The fitting 26 and associated threaded rings 26a, 26b and the connection line 9 are also of a temperature and corrosion-resistant material, in particular of plastics.

The connection line branch 9b has a first blocking or regulation valve V in the control block 5, the valve member of which opens the branch 9b above a certain pressure or pressure range in the reaction chamber 2 with increasing pressure or closes it with decreasing pressure. The valve body of this valve V can be acted upon through the force of a spring e.g. a plate spring 29 or a spiral spring into its blocking position and can be opened through the pressure in branch 9b. In parallel therewith in the control block 5 two or three bypasses are arranged, in which respective control valves are arranged. An electrically operable valve V1 is associated with a first bypass 9b1 and a preferably smaller cross-sectional, which valve is electrically driven (open/close) or regulated in dependence of the pressure in the reaction chamber 2 in such a way that a certain pressure is not exceeded or a desired pressure value is maintained. A pressure-safety valve V2 is associated with a second bypass 9b2, which valve opens preferably abruptly above a higher, predetermined pressure in the reaction chamber 2. In the present embodiment this valve V2 is a rupture disk, which ruptures when the above-mentioned safety pressure value is exceeded and thus opens the bypass 9b2. The branch 9b is preferably dimensioned to be larger in cross-section than the first bypass 9b1. The second bypass 9b2 is preferably dimensioned to be larger still than the branch 9b.

Preferably a further bypass 9b3 is provided in which an electrically or preferably manually operable valve V3 is arranged, which as a further safety valve serves for the purpose of reducing the pressure in the reaction chamber after a treatment process, by opening the valve, thus enabling the access to the reaction chamber, in the event that the preferably programm controlled valve V1 should not function, with which is also possible to reduce the pressure after the treatment process.

The bypasses 9b1, 9b2, 9b3 are arranged in parallel to one another, i.e. each bypass can function independently of the others, which is ensured by the parallel connection.

In the control block 5 there is also arranged a pressure sensor P1 for detecting the pressure in the reaction chamber 2, arranged in particular in the region of the connection line 9, which faces the housing 11.

In the region away from the housing 11 the bypasses are rejoined to the common connection line branch 9b, the connection line branch 9b discharging into a container or chimney (not shown) in the further course of the discharge direction (see arrow 29).

The material to be treated, in particular specimen material 31, can be introduced loose or preferably in one or several receptacles 7 into the reaction chamber 2. In the present embodiment there are shown two receptacles 7 which are open on the upper side, are in particular of hollow cylindrical shape and have a level receptacle base 7a, in which in addition to the specimen material 31 an additional material e.g. a reaction promoting material, in particular a solid or liquid chemical 32 is further arranged. The horizontal cross-sectional size, in this case the diameter of the like receptacles 7, is only a fraction of the cross-sectional size of the reaction chamber 2, so that between the outer circumferential walls of an individual receptacle 7 and the inner circumferential walls of the reaction chamber 2, or between the latter and several receptacles 7 and between the receptacles, there is a free space which is preferably filled with a microwave absorbent, in particular liquid, indirectly effective heating agent, in the present embodiment water 33, up to approximately the height of the filling level of the receptacles 7.

Preferably a further indirectly effective heating agent of microwave-absorbent material is provided, which in the present embodiment is a level heating plate 34, which rests on the preferably level upper side of the housing base 17d and on the level upper side 34a of which the receptacle(s) 7 are in extensive physical contact and thus in large-area heat conducting contact.

The function of the device 1 is as follows:

For the treatment, in particular the preparation of the material 31 this is introduced into the reaction chamber 2 as described above and the housing 11 is closed. Thereafter the treatment of the material 31 under excess pressure and heat can begin, whereby the excess pressure, the heat and the treatment can be controlled automatically or manually.

For a treatment process the loading device 4 is firstly switched on, in order to generate an initial pressure in the reaction chamber 2, in the present exemplary embodiment an initial pressure of e.g. 80 to 100 bar, which can be maintained through switching on the loading device 4 for a certain time or through the pressure sensor P1 or a further pressure sensor. The pressure is generated through introduction or pumping in of air or a gas, e.g. an inert gas such as nitrogen. Thereafter the heating device 3 is switched on, whereby in the present case the material is heated by microwaves directly from below (in as far as the material concerned is a microwave absorbent material) and the heating agent 33 and the heating plate 34 is likewise directly heated. On account of evaporation or reaction of material there is a significant increase in pressure and temperature in the reaction chamber 2 or in the pressure chamber, whereby the material treatment is performed under these conditions.

Devices are provided with which certain temperature and/or pressure values or temperature and pressure ranges can be set or regulated, in order to be able to carry out the treatment at a certain pressure and/or a certain temperature. Thereby it must be taken into account that with regard to the effects of the above-mentioned measures, there are cross-over effects since the temperature may influence the pressure just as the pressure may influence the temperature (taking into account material reactions).

It is advantageous to associate a processor with the control device 6 of the device 1 and to control the device in accordance with a program in such a way that a material treatment can be automatically performed.

Below, regularly occurring operating process steps or operating process steps which are possible in dependence on pressure and temperature development will be described as an advantageous exemplary embodiment.

In a first processing step a loading pressure which may range from zero to 150 bar is generated in the reaction chamber 2 as a starting condition, by switching on the pump 20. Hereby, an initial gas pressure may be generated which may e.g. be approximately 80 bar.

After reaching the loading pressure, which is detected by means of the pressure sensor P1 which delivers a corresponding signal to the control device 6, the heating device 6 is switched on as processing step two and the material is heated directly or indirectly in the above-described manner. An excess pressure is thereby generated in the reaction chamber 2, in a range up to approximately 150 bar with a simultaneous rise in temperature, whereby the treatment process takes place or is forced. With an excess pressure of e.g. approximately 120 bar the pressure sensor P1 supplies a further pressure signal for the regulation of the electrically controllable valve V1, which in consideration of the pressure desired-value of 120 bar is actuated in the opening direction and in the blocking direction so that the desired pressure value is maintained. With this second processing step the heating power is also controlled or regulated (switch on/switch off) in accordance with a desired temperature value so that the desired temperature value is not exceeded, preferably maintained.

In the case in which the pressure in the reaction chamber 2 exceeds the desired pressure value (120 bar), e.g. on account of a strong process reaction, as a further process step three the heating power is reduced or switched off, e.g. at a pressure value of 140 bar.

In addition, as a further process step four, the pressure limiting valve V is provided, which operates at a pressure higher than the desired pressure value, e.g. at approximately 150 bar, and limits the pressure to this pressure value. The pressure-limiting valve V can be regulated in such a way that it operates only when the regulation or controlling of the valve V1 or the temperature regulation or control fails.

As a further safety valve, in accordance with the next process step five, the safety valve V2 is provided, which for the purpose of explosion protection opens or ruptures upon a sudden large pressure increase.

After completion of the process, the housing or reaction chamber 2 is to be subject to pressure release, in order to make access possible. In accordance with a further process step six, this can be achieved through opening the controllable valve V1 or valve V3. The valve V3, which is arranged in the additional bypass 9$b$3, is preferably a manually operable valve in order to be able to perform the pressure reduction even in the event that the valve V1 fails to function.

The control block 5, which is preferably pre-installable as a constructional unit B, is of pressure-resistant metal, in particular of steel. For the purpose of corrosion protection the channels 9$b$, 9$b$1, 9$b$2, 9$b$3 present in the control block 5 are lined with corrosion-resistant plastics. This may be effected in an advantageous manner in that firstly the channels are bored and are then lined with the plastics material, in particular by injecting the plastics. It is also possible to bore out the channels after their lining or to fill them with the plastics and then to bore out the plastics, so that the lining provides the channels.

Below, further details and advantages of the device according to the invention will be described.

The reaction chamber 2 is at the same time the pressure chamber and specimen chamber and it is protected from direct contact between the material and the pressure-resistant pressure wall—in particular of stainless steel —of the housing 11 by means of an insulating lining. The lining is of a plastics, in particular of PTFE, and serves as thermal protection and corrosion protection. The inner lining as well as the circumferential wall can be cooled by means of the cooling device 15, for the purpose of avoiding damage caused by heat. In the reaction chamber, the initial pressure is built up before the beginning of the reaction in order to avoid condensation and losses through evaporation of materials, in particular of solvents. Through the heating of the material 31 with the heating device 3 a further pressure increase to a regulatable operating pressure is achieved. The thus achievable increased boiling points prevent losses of elements and compounds.

With spontaneous exothermal reactions the relatively large overall chamber volume, preferably approx. 3 to 3.5 dm$^3$ provides an additional safety factor, as pressure peaks are avoided. Since, with the present embodiment, on account of the relatively large reaction chamber 2 a large quantity of material 31 can be introduced therein for treatment purposes, a relatively large heat of combustion may be released in the reaction chamber 2 during the treatment, which heat can however be taken up through the heat absorbing capacity of the indirectly effective heating agent 33 and through the relatively large chamber mass, so that temperature peaks arising from this cause are also avoided. Therefore, with the device according to the invention a large quantity of material 31 can be treated without functional problems arising.

With the device according to the invention, the receptacles 7 preferably made of plastics may be of simple and economically producible construction, since they are subjected to the same pressure conditions inside and outside. Thus, differing reactions are also avoided, in as far as they are dependent on differing pressure conditions. Also losses and entrainments from one receptacle to another are reduced to values which can be practically ignored, as the boiling point of the substances (solvents, additional products etc.) is raised greatly on account of the pressure. I.e. treatments can be undertaken at increased temperatures and, despite this, with a closed system.

The measures according to the invention also lead to an automatic boiling point increase through a pressure increase of the liquid medium which forms the indirect heating agent 33. With an initial or loading pressure of e.g. 100 bar a water boiling temperature of 311° C. results. I.e. only when this temperature is exceeded does an automatic internal pressure increase in accordance with the vapour pressure curve of the heating agent 34 arise. Thus, e.g. at a water temperature of 330° C. a vapour pressure of 129 bar ensues. For the application this means that with use of a low boiling-point heating agent a greater pressure automatically arises in the reaction chamber 2 than the evaporation pressure of the material (or components) 31 to be treated in the receptacle 7.

For example, when using water as indirect heating agent 34 and nitric acid as material 31 to be treated or as auxiliary or reaction material. Boiling point of water approx. 100° C. and boiling point of nitric acid approx. 121° C. In this example the vapour pressure of the water is higher and thus prevents volatilization of nitric acid into the gas phase. Thus, condensation of the nitric acid in particular on the inner walls of the reaction chamber 2 is largely prevented. Only gaseous reaction products can theoretically enter the free reaction chamber space. This applies not only to the above-described decomposition example but to almost all chemical reactions with different solvents. This effect can be designated as automatic pressure compensation or adaptation. On account of the direct heat transformation of the microwave irradiation with solid and/or liquid materials (heating agents 33, 34) a sufficiently rapid regulation is possible, i.e. upon reducing or switching off the microwave power the temperature falls comparatively fast and through the control of the parameters the pressure offers a much higher safety standard with a faster reaction than conventional systems.

For the above-described partially microwave absorbing material, a plastics is preferably suitable, in which material components such as particles of microwave-absorbent material, in particular graphite, are mixed or compounded, and which is known under the designation Weflon.

For the lining, sleeve 28 and the heating plate 34 and if appropriate for the base part 17e, a corrosion-resistant material is required which is resistant to acids developing during the treatment of the specimen material, preferably polytetrafluoroethylene (PTFE/Teflon) or tetrafluoro-mixpolymerisate (TFM) or also quartz, ceramic or glass.

Figure 3:
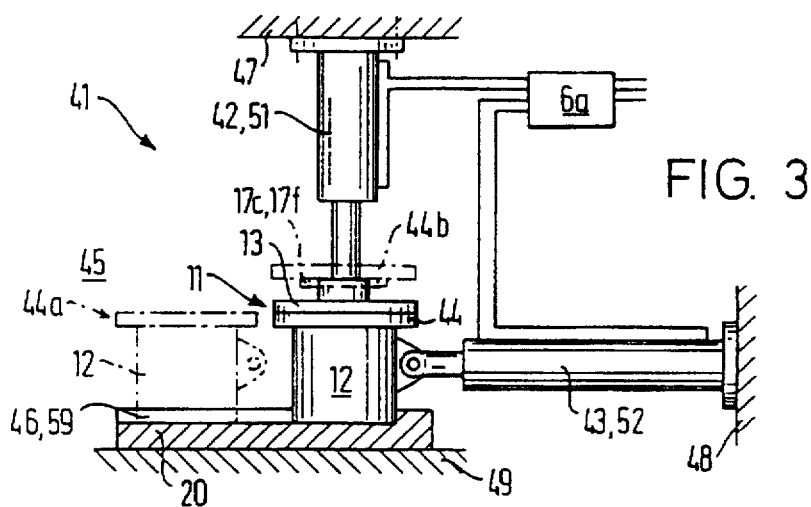
FIGS. 3 to 5 are fragmentary views which show, in schematic, modifications of a lid and container actuation arrangement according to the present invention.
Figure 4:
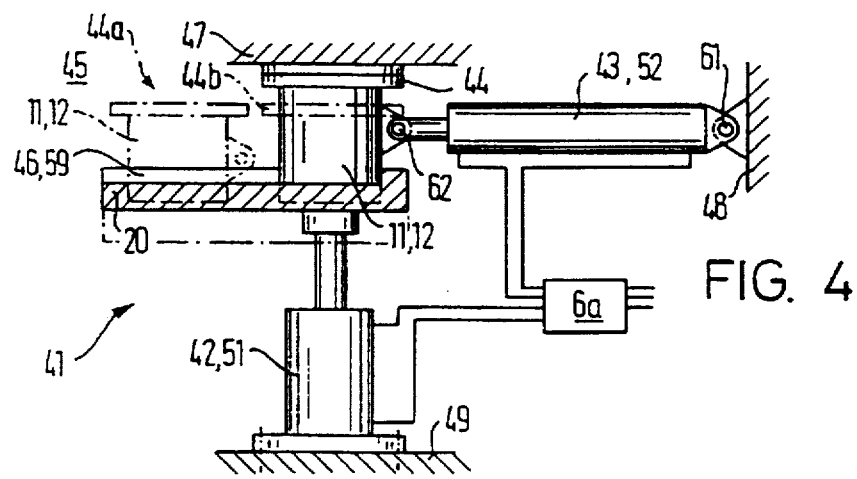
Figure 5:
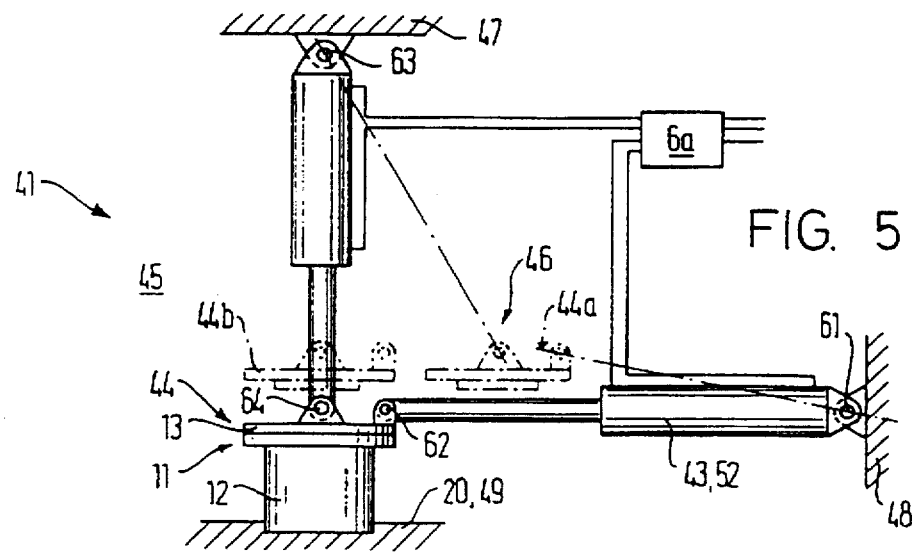

With the exemplary embodiments in accordance with FIG. 3 to 5, the devices 1 can be of the above-described construction and function. The details of the device 1 illustrated in FIGS. 1 and 2 are not illustrated in FIGS. 3 to 5 for reasons of simplicity, as these embodiments are primarily to illustrate a displacement device, generally designated as 41, for the housing 11, with which the housing underpart 12 is easily and conveniently accessible for loading with specimen material or specimen receptacles 7 or auxiliary means 33, 34.

The main parts of the displacement device 41 are an approximately vertically effective lifting device 42 and an approximately horizontally effective displacement device 43, with which a firstly approximately vertical and then lateral relative movement between the housing underpart 12 and the lid 13 can be brought about, such that in its loading position 44a, schematically illustrated in FIGS. 3 to 5, the housing underpart 12 is with regard to the lid 13 relatively laterally displaced towards the operating side 45 and is thus readily accessible from above. With the lifting device 42, which in the embodiments in accordance with FIGS. 3 and 5 engages on the lid 13 and engages into the housing underpart 12 in accordance with FIG. 4, these parts of the housing 11 may be separated from one another in an approximately vertical direction so that even if the lid 13 engages into the housing underpart 12 with a lower-side projection 17c, 17t, a relative lateral displacement of these parts from each other is possible. The latter may in each case be brought about by means of the displacement device 43, which in accordance with FIGS. 3 and 4 engages into the housing underpart 12 and in accordance with FIG. 5 engages at the lid 13. A guide 46, in which the housing underpart 12 (FIGS. 3 and 4) or the lid 13 (FIG. 5) is movably guided for the relative lateral displacement, may be afforded through the cooperation of the lifting device 42 and the displacement device 43, as is shown e.g. in FIG. 5 or it can also be provided as a particular guide element as is shown in FIGS. 3 and 4.

In accordance with FIGS. 3 to 5, there are further provided the supporting part 20 for the housing 11, and abutments 47, 48, 49 for the lifting device 42 the displacement device 43 and the supporting device 20 for their support. The supporting part 20 and the abutments 47, 48, 49 can be parts of an apparatus into which the device 1 is integrated.

With the exemplary embodiments in accordance with FIGS. 3 to 5 the lifting device 42 and the displacement device 43 are formed by respective pneumatic or hydraulic piston cylinders 51, 52 which can be acted upon in both displacement directions. With the embodiment in accordance with FIG. 3 the piston cylinder 51 forming the lifting device 42 is arranged coaxially between the lid 13 and the associated abutment 47 in an approximately vertical position, with the housing 11 closed. The piston cylinder 52 which forms the displacement device 43 engages on the housing underpart 12, whereby it is on the side away from the operation side 45 and extends in approximately horizontal direction. The piston cylinder 51 is preferably rigidly connected with the abutment 47 and the lid 13, so that an approximately vertical guide 50 is provided for the movement of the lid 13. The approximately horizontal guide 46 for the lateral displacement of the housing underpart 12 can e.g. be formed by a longitudinal recess 59 in the supporting part 20 which is formed as a plate, as is shown in FIG. 3, or the guide 46 can also be formed by the piston cylinder 52. For controlling the piston cylinder 51, 52 a pneumatic or hydraulic control device 6a is provided, which is connected by fluid lines with the double-acting piston cylinder 51, 52 and by control lines with the control device 6. For opening the housing 11 firstly the lid 13 is slightly lifted through a corresponding action upon the piston cylinder 51. Thereafter the piston cylinder 52 is activated and the housing underpart 12 is displaced from its working position 44 shown in continuous lines approximately horizontally in the guide 46 into the loading position 44a. The closing of the housing 11 occurs in reversed displacement or control steps, i.e. firstly the housing underpart 12 is displaced back into its working position 44 and then the lid 13 is lowered from its ready position 444b into the closing position.

The exemplary embodiment in accordance with FIG. 4 differs from the above-described embodiment in that the lid 13 is fixedly fastened to the abutment, e.g at the abutment 47, and the supporting part 20 is in this case approximately vertically displaceable by means of the lifting device 42 which is e.g. also formed by a piston cylinder 51. In this embodiment it is advantageous to mount the piston cylinder 52 which forms the displacement device 43 in joints 61, 62 with joint axes running at right angles to the vertical plane of movement, between the housing underpart 12 and the associated abutment 48. With this arrangement, for opening the housing 11, the housing underpart 12 is slightly lowered into the ready position 44b and then the housing part 12 is displaced by means of the piston cylinder 52 into the loading position 44a. The closing of the housing 11 occurs with reversed displacement or control steps.

The exemplary embodiment according to FIG. 5, according to which the same or similar parts are also designated with the same reference signs, differs from the exemplary embodiment according to FIG. 3 in that the lifting device 42 and the displacement device 43 or both piston cylinders 51, 52 engage on the lid 13 and also the piston cylinder 51 which forms the lifting device 52 is mounted in joints 63, 64 with joint axes running at right angles to the vertical plane of movement of the lid 13. The displacement control of the piston cylinders 51, 52 corresponds therewith, whereby however only the lid 13 is firstly displaced into the ready position 44b and then into the open position or loading position 44a away from the operating side 45. On account of the double coupling of the lid 13 an integrated guide 46 results in this case. The piston rod of the piston cylinder 51 can be pushed out upon movement into the open position 58 or can be pulled out by the piston cylinder 52. The closing movement occurs correspondingly in reversed displacement steps.

Figure 6:
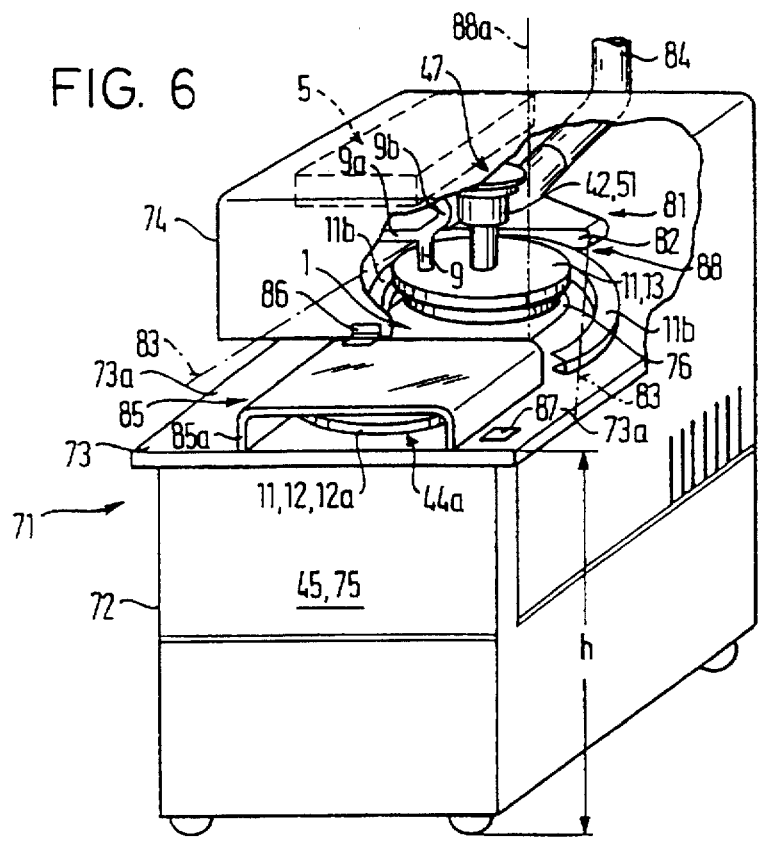
FIG. 6 is a perspective view, partially in section, of a heating device according to the present invention which incorporates the lid and container actuation arrangement of FIG. 3.
Figure 7:
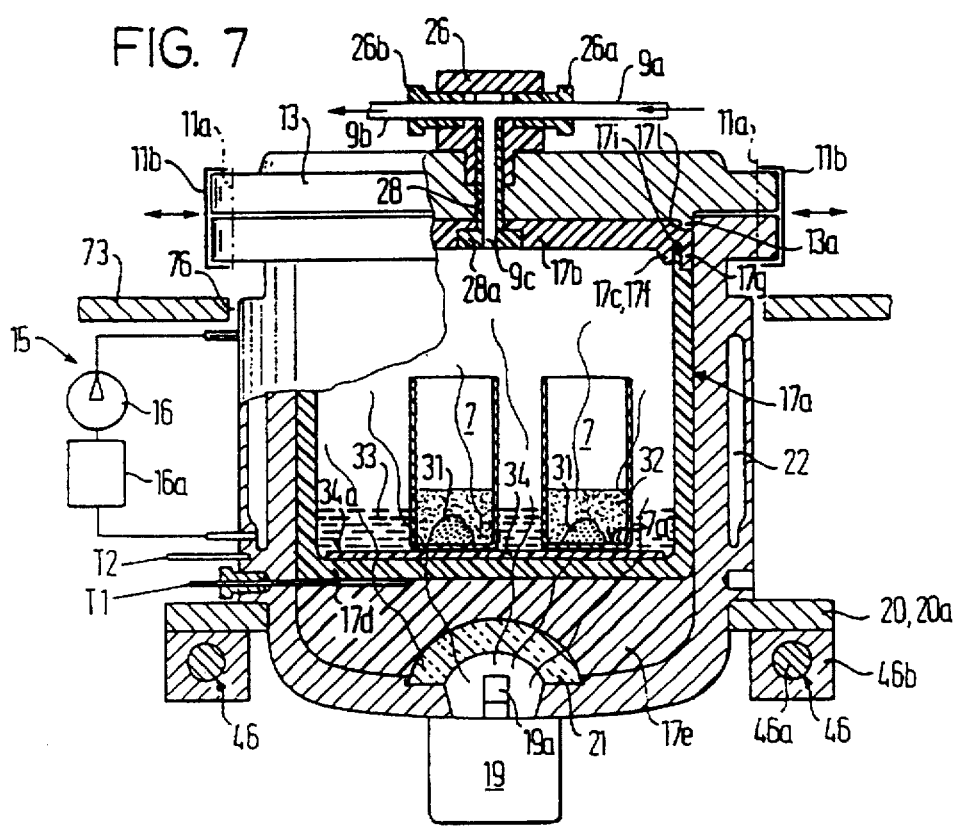
FIG. 7 is an elevational view, partially in section, showing a reaction chamber used in the heating device of the present invention.

The apparatus in FIG. 6, generally designated as 71, with the integrated device 1, has a quadratic housing 72 which in its forward region, towards the operating side 45, has an approximately horizontal working plate 73 of a height h, approximately that of a table. In its rearward region the housing 72 is heightened in stepped manner through an assembly 74. The integration or arrangement of the device 1 in the apparatus 71 is such that the housing 11 is in the rear region thereof when in its working position, i.e. below the assembly 74, whereby the housing underpart 12 is displaceable towards the operating side 45 into the forward region of the apparatus 71, so that in the loading position 44a it is in the vicinity of the forward side 75 of the housing 72 and its edge flange 12a is in the region of the working plate 73, preferably projecting slightly upwardly above this plate. For this purpose the working plate 73 has an elongate aperture 76 which extends forwardly from the rear, the elongate aperture mid-points of which are in the working position 44 and in the loading position 44a for the housing underpart 12. Of the displacement device 41, in FIGS. 6 and 7 only the lifting device 42 for the lid 13 and parts of the displacement device 43 for the housing underpart 12 are shown, namely the supporting part 20 in the shape of a carrier ring 20a, in which the underpart of the housing 12 is positioned with a stepped taper on the lower side, and the guide 46, here in the form of two guide rods 46a which are arranged on the two sides of the housing underpart 12, on which the carrier ring 20a is mounted with running sleeves 46b to be freely displaceable by hand between the working position 44 and the loading position 44a. In order to enable the displacement movement of the housing underpart 12 and the lid 13, the signal, control and supply or discharge lines extending thereto are formed flexibly, as in the embodiments according to FIGS. 3 to 5. The guide rods 46a are mounted in their end regions in the housing 72. Of the device 42 the piston cylinder 51 is visible in FIG. 6. The abutment 47 associated therewith is part of the apparatus 71 or of its housing 72 and can e.g. be formed by a tie bar and/or the upper wall of the housing 72.

A suction device 81—not shown in FIGS. 1 to 5—is associated with the device 1 in all present embodiments, for drawing off the vapours which emerge from the opened housing 11. The suction device 81 has a suction opening 82 which is arranged behind the housing 11 at the height of the opening slit which is formed upon the opening of the lid 13, preferably in the form of a horizontal, transversely extending slit, to generate a broad suction stream 83 which extends approximately horizontally, covering the entire width of the opening of the housing underpart 12 and preferably being so strong that it may also draw off the vapours which emerge from the housing underpart 12 in the loading position 44a, in the present embodiment from the front to the rear. The drawn off vapours can be discharged through a continuing discharge line 84, passing through the housing 72 to the outside, outside the building present, or to a chimney (not shown).

A guide sheet 85 extending approximately horizontally is provided on the one hand for improvement of the draw-off, and as a mechanical safety device on the other hand, which is positioned at a small spacing of approximately of few cm above the opening of the housing underpart 12 in the loading position 44a and is mounted displaceably between its working position covering the opening and a release position which exposes the opening. With the present embodiment the guide plate 85 is arranged to be upwardly tiltable from the opening, e.g. to the side or in accordance with FIG. 6 to the rear. For this purpose, there may serve hinges 86, which in the present embodiment are arranged between the rear end of the guide sheet 85 and the neighbouring front side of the assembly 74 and are fastened thereto. Preferably the guide sheet 85—viewed from the front—with laterally angled limbs 85a, has the cross-sectional shape of a U standing on its head, so that the spreading of the emerging vapours to the sides is hindered and the guidance of the suction stream 83 and the suction is improved. The lateral limbs 85a preferably stand on the working plate 73. In its covering working position the guide sheet 85 protects the open housing underpart 12 not only from impurities, which might fall into it, but it is also a protection device against the danger of the hands of the operating person being squashed when the housing underpart 12 is displaced into the loading position 44a. Therefore it is advantageous for safety reasons to design the controller of the device 1 in such a way that the housing underpart 12 can be displaced into the loading position 44a only in the working position of the guide sheet 85. This may be realized by means of a contact maker 87 on the housing, which is actuated by the guide sheet 85 in its working position and is connected with the corresponding control device 6, 6a by means of a signal line.

The guide sheet 85 preferably consists of transparent material, in particular of plastics, such as plexiglas or the like, to enable viewing into the housing underpart 12.

The broad surface parts 85a of the working plate 73, present to the two sides of the guide sheet 85, may serve as placement surfaces e.g. for specimen receptacles 7.

The closure ring halves 11b, which are also present in FIG. 6, can be actuated by a drive motor. They can each be pivotally mounted at their respective ends in a joint 88 with a vertical joint axis 88a, which is preferably arranged behind the housing 11 and is fastened to the housing 72 or to components attached thereto. The drive motor (not shown) can be arranged in the region of the joint 88 or can be integrated therein. Before the opening of the housing 11 by means of the lifting device 42 the closure ring halves 11b or another closure means are to be released, and upon closure are to be closed after the lifting movement.

Preferably the conductive housing underpart 12 which is in particular of corrosion-resistant material such as metal, in particular stainless steel, is fabricated in one piece with its base 14 and is continuously connected thereto, whereby it is very stable.

I claim:

1. A device for initiating and/or promoting chemical or physical processes in a material, said device comprising:
- a reaction chamber which is surrounded by a housing;
- a microwave heating means arranged to heat material in the reaction chamber;
- said housing comprising a pot-shaped housing underpart and a lid;
- and a lifting device for changing the relative vertical positions of the housing underpart and the lid whereby in one relative position the lid covers the housing underpart and in another relative position the lid is removed from the housing underpart;

characterized in that:
- said device includes a horizontal actuating device for changing the relative horizontal positions of the housing underpart and the lid whereby in one relative horizontal position the lid and housing underpart are vertically aligned with each other and in another relative horizontal position the lid and housing underpart are relatively horizontally displaced from each other;
- said device includes a housing movement control which controls the relative movement of the housing underpart and the lid such that, upon opening of the housing, the lifting device begins to function prior to operation of said horizontal actuating device so that relative horizontal displacement of the housing underpart and lid occur after the lid is removed from the housing underpart; and
- the relative displacement of the housing underpart and the lid is such that the housing underpart with the lid removed is located towards a loading side of the device.

2. A device according to claim 1 wherein said lifting device lifts and lowers said lid and said horizontal actuating device produces horizontal movement of said housing underpart.

3. A device according to claim 1 wherein said lifting device lifts and lowers said housing underpart and said horizontal actuating device produces horizontal movement of said housing underpart.

4. A device according to claim 1 wherein said lifting device lifts and lowers said lid and said horizontal actuating device produces horizontal movement of said lid.

5. A device according to claim 1 characterized in that,
- the lid is provided on its lower side with a projection which is engagable with a lower-side projection in the housing underpart,
- and in that the extent of the vertical lifting and lowering movement is greater than the height of the projection.

6. A device according to claim 1, characterized in that,
- there is provided a suction device for drawing off vapors which emerge when the housing is open, whereby relative to the housing, the suction device is arranged away from the guide.

7. A device according to claim 1, characterized in that,
- there is provided a generally horizontal guide plate in association with an opening of the housing underpart in its loading position, which guide plate is spaced above the opening and is displaceable between a working position which covers the opening and a release position which exposes the opening, said guide plate being tiltable away from said opening.

8. A device according to claim 1, characterized in that:
- there is provided a microwave heating means for the reaction chamber;
- said housing has a gas outlet;
- an outlet valve is associated with said gas outlet, for releasing an interior pressure which exceeds a given value in the reaction chamber; and
- said housing has a gas inlet.

9. A device according to claim 8, characterized in that:
- at least one valve is arranged in a block which is spaced from the housing, said block being connected with the housing by way of a pipe connection.

10. A device according to claim 8 or 9, characterized in that:
- a pressure source and a control device are associated with the inlet for supplying gas under pressure before the heating means is switched on.

11. A device according to claim 10, characterized in that:
- the gas outlet and gas inlet are formed by a common passage in the housing and by means of a gas line which is connected to the passage, which line branches on the one hand to an outlet valve and on the other hand to a pressure source.

12. A device according to claim 8, characterized in that:
- at least one of the outlet and inlet is arranged in the lid of the housing.

13. A device according to claim 1, characterized in that:
- the housing is made of metal and is internally lined with a corrosion-resistant and heat-resistant material.

14. A device according to claim 1, characterized in that,
- a heating agent is arranged between the coupling device for microwaves and the reaction chamber, said heating agent being indirectly effective upon the material.

15. A device according to any claim 1, characterized in that,
- there is provided at least one receptacle for material to be heated in the reaction chamber, said receptacle being placeable in the reaction chamber.

16. A device according to claim 1, characterized in that,
- the exterior cross-sectional size of the receptacle is smaller than the horizontal cross-sectional size of the reaction chamber.

17. A device according to claim 1, characterized in that,
- there is provided a heating agent which is capable of absorbing microwave energy, said heating agent being in broad surface contact with one of the material and the receptacle in the reaction chamber.

18. A device according to claim 1, characterized in that:
- a plate-like supporting element is provided on the base of the reaction chamber, said supporting element being arranged to carry one of the material and the receptacle, said material being capable of absorbing microwave energy.

19. A device according to claim 1, characterized in that:
- there is provided a coupling device for coupling microwaves from below into the reaction chamber.

20. A device according to claim 1, characterized in that:
- there is provided a regulation device which is arranged to regulate the interior pressure in the reaction chamber in dependence upon at least one of the interior pressure and the inferior temperature, said regulation device including an outlet valve.

21. A device according to any claim 1, characterized in that:
- there is provided a regulation device to regulate the temperature in the reaction chamber, said regulation device being operative to switch heating power on and off according to the temperature in the reaction chamber.

22. A device according to claim 1, characterized in that:

said outlet line is provided with a first bypass in which a valve is arranged, said valve being controlled to regulate the interior pressure.

23. A device according claim 1, characterized in that:

the outlet valve has associated therewith a second bypass, in which there is arranged a safety valve which opens automatically at an increased interior pressure.

24. A device according to claim 1, characterized in that:

at least one valve is provided in a further bypass for pressure release of the reaction chamber after a process is completed in the reaction chamber.

25. A device according to claim 1, characterized in that:

a regulatable valve is associated with the reaction chamber for releasing initial pressure before opening the reaction chamber.

* * * * *